United States Patent
Kashiwagi

(10) Patent No.: US 7,746,975 B2
(45) Date of Patent: Jun. 29, 2010

(54) BREAST'S RADIATION IMAGE TAKING APPARATUS AND A METHOD OF TAKING A BREAST'S RADIATION IMAGE

(75) Inventor: Nobuhiko Kashiwagi, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 11/865,017

(22) Filed: Sep. 30, 2007

(65) Prior Publication Data
US 2008/0080667 A1    Apr. 3, 2008

(30) Foreign Application Priority Data
Sep. 29, 2006    (JP)    ............................. 2006-267793

(51) Int. Cl.
*A61B 6/04*    (2006.01)
(52) U.S. Cl. ................................. 378/37; 378/62; 378/95
(58) Field of Classification Search ................. 378/37
See application file for complete search history.

(56) References Cited

U.S. PATENT DOCUMENTS 5,712,890 A * 1/1998 Spivey et al. ................. 378/37
6,934,409 B2 * 8/2005 Ohara ........................ 382/132

* cited by examiner

*Primary Examiner*—Hoon Song
*Assistant Examiner*—Mona M Sanei
(74) *Attorney, Agent, or Firm*—Sughrue Mion, PLLC

(57) ABSTRACT

The breast's radiation image taking apparatus and method set an imaging condition in association with a first region on a distal end side which is an imaging region spaced from a chest wall of a subject, take a first radiation image of the breast in the first region and take a second radiation image of the breast in a second region on a proximal end side closer to the chest wall than the first region under the same imaging condition as in the first region. The apparatus includes a radiation source, a breast support plane on which the breast is to be placed, a radiation-receiving plane for acquiring a radiation image of the breast, an imaging position switching device by which relative positions of the both planes are changed, an imaging condition setting device for setting an imaging condition and an imaging control device controls so that the first and second radiation images are taken in two positions on both sides.

18 Claims, 7 Drawing Sheets

BREAST'S RADIATION IMAGE TAKING APPARATUS AND A METHOD OF TAKING A BREAST'S RADIATION IMAGE

The entire contents of documents cited in this specification are incorporated herein by reference.

BACKGROUND OF THE INVENTION

The present invention relates to the technical field of taking a breast's radiation image, that is, mammography, more particularly, to a breast's radiation image taking apparatus, that is, a mammography apparatus, that enables the radiation image of a large breast to be taken on a small radiation-receiving plane, as well as a method of taking a breast's radiation image, that is, a mammography.

In breast cancer screening, the success rate of early detection that is achieved through physical examination by inspection and palpation only is improved if it is combined with mammography by a radiation image taking apparatus solely intended for breasts (which is hereinafter referred to as a breast imaging apparatus); hence, breast cancer screening that is currently practiced involves the use of a breast imaging apparatus in addition to (or in place of) inspection and palpation.

The breast imaging apparatus comprises an imaging table enclosing a radiation image recording medium (which is hereinafter referred to as an imaging medium); to operate it, the breast is placed on the imaging table, compressed with a press plate, irradiated with a radiation from the press plate side; the radiation transmitted through the breast is received by the imaging medium and its radiation image is taken on the imaging medium.

The conventional breast imaging apparatus has been such that a radiation image converting panel (commonly called IP) that employs a stimulable phosphor or an X-ray film is used as the imaging medium and accommodated in a light-shielding case called a cassette, which in turn is loaded at a specified position in the imaging table for taking a radiation image of the breast.

A new model of breast imaging apparatus is recently increasing in number; an IP, a means of reading the radiation image taken/recorded on the IP, and a detector called a flat panel detector that performs conversion (photoelectric conversion) of a radiation to an image are fixedly installed within the imaging table and a radiation image that is taken of the breast is displayed on a screen or transferred to an external computer.

SUMMARY OF THE INVENTION

The breast size differs from one woman to another and if a large breast is compressed with a press plate, part of it may sometimes extend beyond the radiation-receiving plane.

In the case of a breast imaging apparatus of the type that is to be loaded with a cassette-accommodated imaging medium, replacement of imaging tables is simple and various sizes of breasts can be imaged by employing accordingly sized imaging tables that accommodate accordingly sized imaging media.

However, in the case of a breast imaging apparatus that has an imaging medium such as IP, a flat panel detector, etc. fixedly installed in the interior of an imaging table (this type of apparatus is hereinafter referred to as a built-in type), it is difficult to replace imaging tables in accordance with a specific breast size.

Imaging media for taking/recording the radiation images of breasts usually come in two sizes, 18×24 cm and 24×30 cm. When performing MLO imaging (mediolateral and oblique imaging), the position of the breast of a woman being examined may sometimes deviate from the optimum imaging position depending upon her physique or the size of her breast. This inconvenience is less likely to occur with a smaller imaging table. Hence, most hospitals, if they are to be equipped with any built-in breast imaging apparatus, choose imaging media of the smaller 18×24 cm size and this further increases the likelihood that a large compressed breast partly extends beyond the light-receiving plane of the imaging medium.

The present invention has been accomplished in order to solve the aforementioned problems of the prior art.

An object of the present invention is to provide a breast's radiation image taking apparatus which, even if a compressed breast partly extends beyond the light-receiving plane of an imaging medium such as an IP or a flat panel detector, can perform appropriate taking of a radiation image of the breast.

Another object of the present invention is to provide a method of taking a breast's radiation image.

In order to achieve the above objects, the present invention provides a breast's radiation image taking apparatus, comprising:

a radiation source for irradiating a breast of a subject;

a breast support plane on which the breast is to be placed;

a radiation-receiving plane for acquiring a radiation image of the breast;

an imaging position switching means by which relative positions of the breast support plane and the radiation-receiving plane are changed so that a position of the radiation-receiving plane is switched between a proximal end side which is near a chest wall of the subject and a distal end side which is more spaced from the chest wall than the proximal end side;

an imaging condition setting means for setting an imaging condition in accordance with imaging of a first radiation image for the case where the radiation-receiving plane is positioned on the distal end side; and an imaging control means that allows the imaging position switching means to switch the position of the radiation-receiving plane from the proximal end side to the distal end side or vice versa so that the first radiation image and second radiation image of the breast are taken in two positions on both the proximal and distal end sides.

In the breast's radiation image taking apparatus of the present invention, the imaging control means preferably performs first imaging of the first radiation image with the radiation-receiving plane positioned on the distal end side, then preferably allows the imaging position switching means to switch the position of the radiation-receiving plane, and preferably performs second imaging of the second radiation image with the radiation-receiving plane positioned on the proximal end side.

In a preferred embodiment of the breast's radiation image taking apparatus, two imaging modes are set, one being a split imaging mode in which the first and second radiation images are taken with the position of the radiation-receiving plane being switched from the distal end side to the proximal end side or vice versa and the other mode being a normal imaging mode in which the second radiation image is preferably only taken with the radiation-receiving plane being positioned on the proximal end side, and the imaging condition setting means, when in the normal imaging mode, preferably sets the imaging condition in accordance with the imaging for the case where the radiation-receiving plane is positioned on the proximal end side.

The imaging position switching means preferably switches the position of the radiation-receiving plane as relative to the breast support plane by moving the radiation-receiving plane.

The present invention also provides a breast's radiation image taking method, comprising the steps of:

setting an imaging condition in association with a first region on a distal end side which is an imaging region spaced from a chest wall of a subject;

taking a first radiation image of the breast in the first region on the distal end side; and taking a second radiation image of the breast in a second region on a proximal end side closer to the chest wall than the first region on the distal end side under the same imaging condition as in the first region on the distal end side.

In a preferred embodiment, the breast's radiation image taking method further comprises the step of:

changing the imaging region from the first region on the distal end side to the second region on the proximal end side by changing relative positions of the breast support plane on which the breast is to be placed and the radiation-receiving plane for acquiring a radiation image between the step of first imaging in the first region on the distal end side and the step of second imaging in the second region on the proximal end side.

The relative positions of the breast support plane and the radiation-receiving plane are preferably changed by moving the radiation-receiving plane from first position associated with the first region on the distal end side to second position associated with the second region on the proximal end side.

The second region on the proximal end side preferably partly overlaps the first region on the distal end side by a specified amount.

In the breast's radiation image taking apparatus, the second region on the proximal end side preferably partly overlaps the first region on the distal end side by a specified amount.

In a preferred embodiment, the breast's radiation image taking apparatus further comprises: an imaging table on an upper surface of which the breast is to be placed to take the radiation image of the breast, in which the breast support plane is preferably the upper surface of the imaging table.

In a preferred embodiment, the breast's radiation image taking apparatus further comprises: a detector for acquiring the radiation image of the breast, and being contained in an interior of the imaging table, in which the radiation-receiving plane is preferably a receiving plane of the detector.

In a preferred embodiment, the breast's radiation image taking apparatus further comprises: a detector for acquiring the radiation image of the breast, in which the radiation-receiving plane is preferably a receiving plane of the detector.

The detector is preferably an imaging medium for recording a radiation image.

The detector is preferably a radiation image conversion panel utilizing a stimulable phosphor or a flat panel detector for acquiring the radiation image by radiation-to-image conversion.

According to the present invention having the features described above, even if the breast of a subject to be examined by mammography is so large that it may partly extend beyond the light-receiving plane of an imaging medium such as IP or flat panel detector, a radiation image of the breast is taken both on the distal end side that is spaced from the chest wall of the subject and on the proximal end side in contact with the chest wall and by performing such split imaging, a radiation image of the breast can be obtained for all of its areas.

The breast has a mammary gland in which the lactiferous ducts are concentrated toward the apex (mammary papilla) and most breast lesions develop in that area. Hence, a mammogram which is a radiation image of the breast often has important information recorded on the apex side. In the present invention, an imaging condition is set in association with the distal end side which corresponds to the apex side of the breast and irrespective of whether the part of the breast that is to be imaged is on the distal or proximal end side, its radiation image is taken under the imaging condition that is set for the distal end side. Therefore, in addition to the advantage that the apex side of the breast that is most likely to contain important information can be imaged under optimum conditions, the two radiation images obtained by split imaging have been taken under identical conditions, so they can be viewed, combined or otherwise processed in an appropriate way.

DETAILED DESCRIPTION OF THE INVENTION

On the pages that follow, the breast's radiation image taking apparatus and method of the present invention are described in detail with reference to the preferred embodiments shown in the accompanying drawings.

Figure 1:
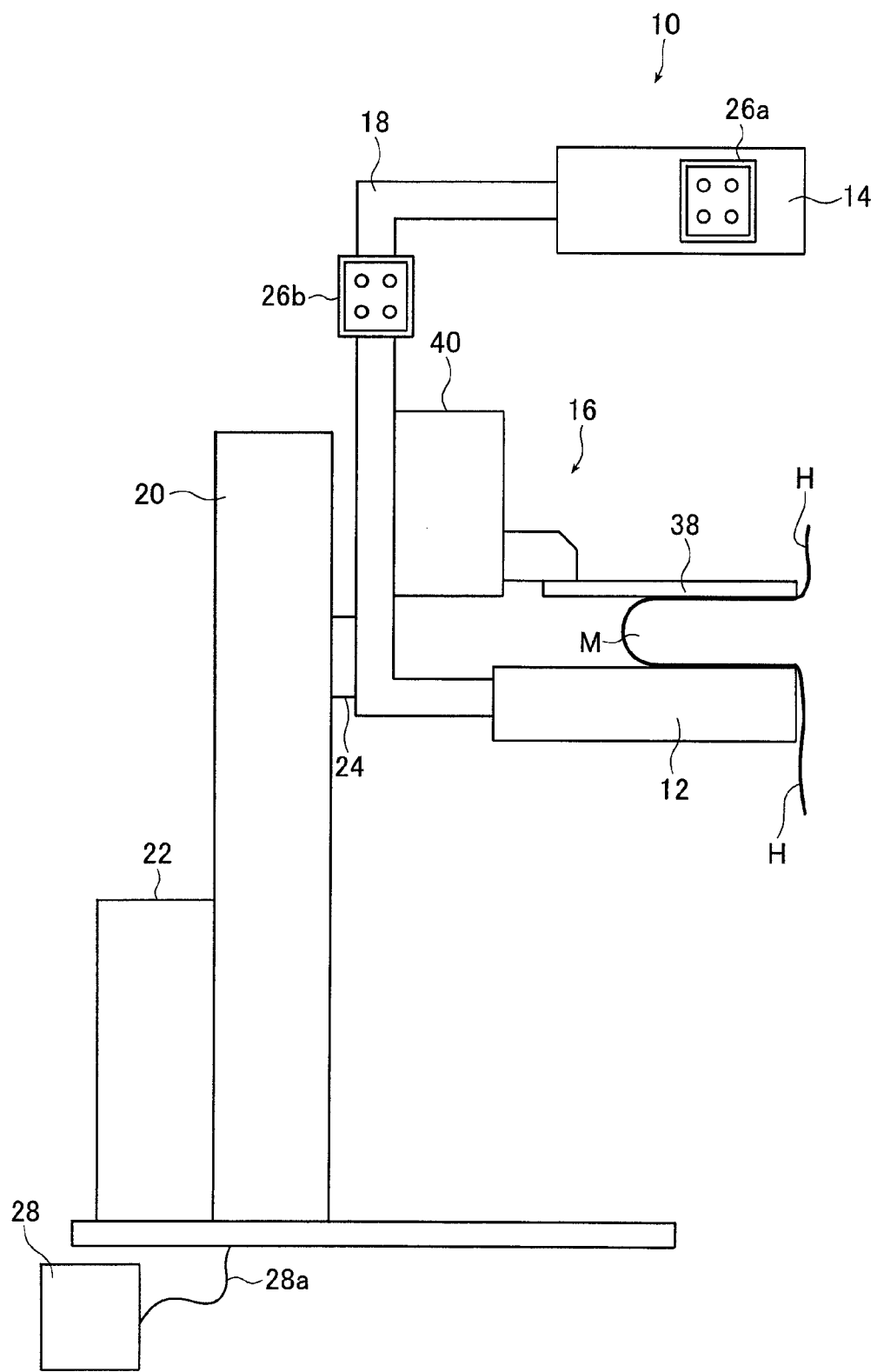
FIG. 1 shows in concept an example of the breast's radiation image taking apparatus of the present invention.

FIG. 1 shows in concept an example of the breast's radiation image taking apparatus of the present invention for implementing the breast's radiation image taking method of the present invention.

As FIG. 1 shows, the breast's radiation image taking apparatus which is generally indicated at 10 (and hereinafter referred to as the breast imaging apparatus 10) is basically composed of an imaging table 12, an irradiating section 14, a compressing means 16, an arm 18, a base 20, and an X-ray irradiating high-voltage power supply 22. The breast imaging apparatus 10 is basically the same as the ordinary breast's radiation image taking apparatus, except that it is capable of split imaging which will be described later in detail.

In the illustrated breast imaging apparatus 10, the arm 18 is bent at right angles in two positions to assume a generally C-shaped form; the upper end of the arm 18 is fixed to the irradiating section 14 and the lower end to the imaging table 12, with the compressing means 16 fixed between the irradiating section 14 and the imaging table 12.

Figure 2:
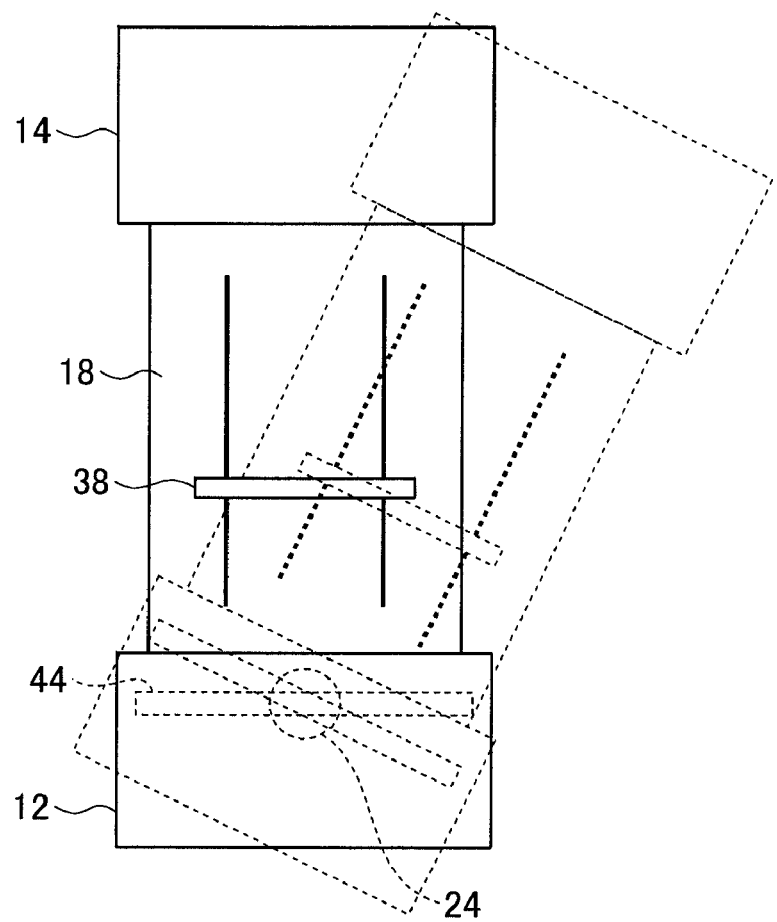
FIG. 2 shows in concept how the breast's radiation image taking apparatus shown in FIG. 1 is operated.

The arm 18 is supported on the base 20 by means of a shaft 24. Built in the interior of the base 20 are a means for rotating the shaft 24, as well as a means for vertically moving it. The arm 18 and, hence, the imaging table 12 and the irradiating section 14 are moved up and down as the shaft 24 is moved up and down by the means that causes it to move vertically; in addition, as shown schematically in FIG. 2, they are rotated as the shaft 24 is rotated by the means that causes it to rotate, whereupon angular adjustment is done to allow for MLO imaging and the like.

The base 20 is fitted with manipulating means 26 (26a and 26b), as well as manipulating means 28 for making a variety of manipulations such as vertically moving and rotating the arm 18 (or shaft 24), and vertically moving a press plate 38 to be described later.

The manipulating means 26a is fitted on a lateral side of the irradiating section 14 and the manipulating means 26b on a lateral side of the arm 18; each of these manipulating means has switches associated with the rotation and vertical movement of the arm 18, a switch that turns on a lamp for illuminating the field of irradiation, and other necessary switches. The manipulating means 28 is a pedal that is connected to the base 20 via a cable 28a and has a switch associated with the vertical movement of the press plate 38, a switch associated with the vertical movement of the arm 18, and other necessary switches.

Figure 3:
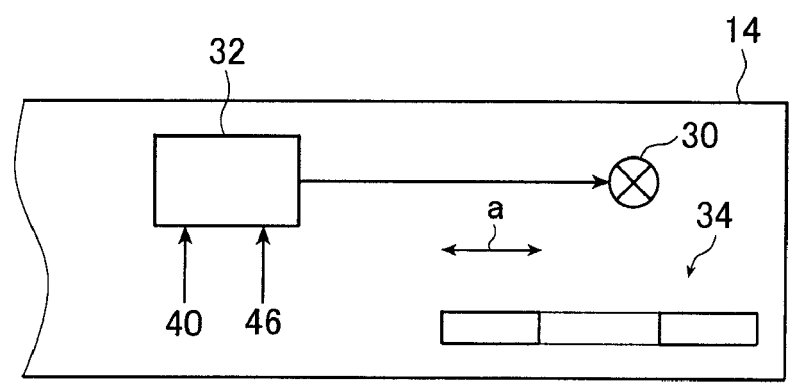
FIG. 3 shows in concept the irradiating section of the breast's radiation image taking apparatus shown in FIG. 1.

The irradiating section 14 is a site for applying a radiation to the breast M and, as shown schematically in FIG. 3, it has a radiation source 30, means 32 for controlling the radiation source 30, and a collimator 34 that regulates the field of irradiation.

In the illustrated case, the collimator 34 is adapted to be capable of moving back and forth as indicated by the two-headed arrow a, so that it moves away from or comes closer to the chest wall H of a subject; in a preferred embodiment, the aperture through which a radiation passes is adapted to be variable in size. Thus, in FIG. 3, the subject (her chest wall H) is positioned on the right side.

The radiation source 30 may be an ordinary radiation source that is conventionally used in radiation image taking apparatuses.

The control means 32 manages and controls the overall operation of the breast imaging apparatus 10. The control means 32 is supplied with the position information about the press plate 38 that comes from a means 40 to be described later for vertically moving the compressing means 16, as well as with the result of radiation detection from an AEC sensor 46 in the imaging table 12. The control means 32 learns the thickness of the breast M under examination from the position information about the press plate 38; it also learns the dose of radiation through the breast M from the result of radiation detection by the AEC sensor 46; as a result, the control means 32 sets an imaging condition for taking a radiation image of the breast M and performs its imaging with the settings of the imaging condition.

It should be noted here that the imaging condition may be set by the same method as employed for the conventional breast's radiation image taking apparatuses; in one example, the quality of radiation (e.g. the tube voltage of the radiation source 30) is determined from the thickness of the breast M and the time of irradiation is determined from the dose of radiation through the breast M.

In the breast imaging apparatus 10, two imaging modes are set, one being a split imaging mode and the other being a normal imaging mode.

The split imaging mode is adapted for imaging the breast M which is so large that it partly extends beyond the (radiation) receiving plane of a detector 44 to be described later; in this mode, two breast images are taken, one over a region on the distal end side which corresponds to the apex side (mammary papilla side) of the breast and the other over a region on the proximal end side which corresponds to the chest wall H side of the breast. The normal imaging mode, on the other hand, is adapted for imaging the normal size of breast M; in this mode, the entire area of the breast is imaged in one step on the proximal end side. These imaging modes are described later in detail.

In the split imaging mode, the imaging region, or the field of irradiation needs to be switched between the distal end side and the proximal end side.

The irradiating section 14 of the breast imaging apparatus 10 shown in FIG. 1 has the radiation source 30 fixed near the terminal of the proximal end side (in a position close enough to the subject) and by moving the collimator 34 either away from or closer to the chest wall H, the field of irradiation is altered. Note here that placing the radiation source 30 on the subject side is preferred since it contributes to minimizing the radiation exposure of the subject.

The compressing means 16 compresses the breast onto the imaging table 12 while it is being imaged; the compressing means 16 has a press plate 38 that compresses the breast onto the imaging table 12 and a means 40 for vertically moving the press plate 38. The press plate 38 and the vertically moving means 40 are basically of known types of a breast press plate and a means for vertically moving it, as they are provided in a known type of breast's radiation image taking apparatus.

In the breast imaging apparatus 10 shown in FIG. 1, the vertically moving means 40, at the time when the press plate 38 has compressed the breast M for imaging it, sends the position information about the press plate 38 to the means 32 for controlling the irradiating section 14. As already mentioned, it is from the supplied position information that the control means 32 learns the thickness of the breast M at the time of its imaging.

In the breast imaging apparatus 10 shown in FIG. 1, the press plate 38 is detachably mounted on the vertically moving means 40. The press plate 38 is available in two sizes, typically 18×24 cm for a breast of normal size and 24×24 cm for a larger breast.

The press plate 38 with the size of 18×24 cm is used in the normal imaging mode, and the press plate 38 with the size of 24×24 cm is used in the split imaging mode.

The vertically moving means 40 is fitted with a means for detecting the type of the press plate 38; the breast imaging apparatus 10 is such that if the press plate 38 with the size of 18×24 cm is attached to the vertically moving means 40, it presumes that the normal imaging mode has been set (commanded or entered) and automatically starts imaging in the normal mode; in contrast, if the press plate 38 with the size of 24×24 cm is attached to the vertically moving means 40, it presumes that the split imaging mode has been set and automatically starts imaging in the split mode. In other words, the attachment of the press plate 38 serves as a means of setting the imaging mode.

The method of detecting the type of the press plate 38 is not limited in any particular way and various known types of means may be employed, as exemplified by a method in which a characteristic projection is provided on each type of the press plate 38 which is attached to the vertically moving means 40 that is provided with a recess that engages the projection and the projection on the attached press plate 38 is detected either mechanically or optically to detect the type of that press plate 38, and a method that uses a bar code and a bar code reader.

The means of setting the imaging mode is not limited to the methods that depend on the type of the press plate 38 and various methods of selecting operating modes may be employed, as exemplified by fitting the manipulating means 26 and 28 with button switches for selecting between the two imaging modes, a dial switch for changing from one imaging mode to the other and vice versa.

The imaging table 12 is a hollow case on the upper surface of which the breast is to be placed during imaging; as shown schematically in FIG. 4, it contains a scattering removing grid 42, a detector 44, and an AEC (automatic exposure control) sensor 46 in its interior. In the breast imaging apparatus 10, the upper surface of the imaging table 12 serves as the plane on which the breast M is to be placed.

The scattering removing grid 42 (which is hereinafter referred to simply as the grid 42) is a known means of removing scattered radiation that is installed in a radiation image acquisition apparatus for the purpose of preventing the incidence of a scattered radiation into the detector 44.

The detector 44 is an imaging medium for taking/recording a radiation image. In the present invention, the detector 44 that can be used is not limited in any particular way and various types of imaging medium (radiation image recording medium) that are employed in radiation image taking apparatuses may be used, as exemplified by the radiation image conversion panel utilizing a stimulable phosphor, that is, so-called the IP (imaging plate) which depends on a stimulable phosphor for radiation image conversion or the flat panel detector which depends on a solid-state detector, a TFT (thin-film transistor) or the like for radiation-to-image conversion (or photoelectric conversion).

If an IP is used as the detector 44, the imaging plate 12 contains in it an IP reading means that applies exciting light to the IP and photoelectrically reads the photostimulated light that has been issued from the IP in response to the admission of the exciting light.

In the illustrated apparatus, the detector 44 may be of the 18×24 cm size which is commonly employed as the smaller size in breast's radiation image taking apparatuses.

Figure 4A:
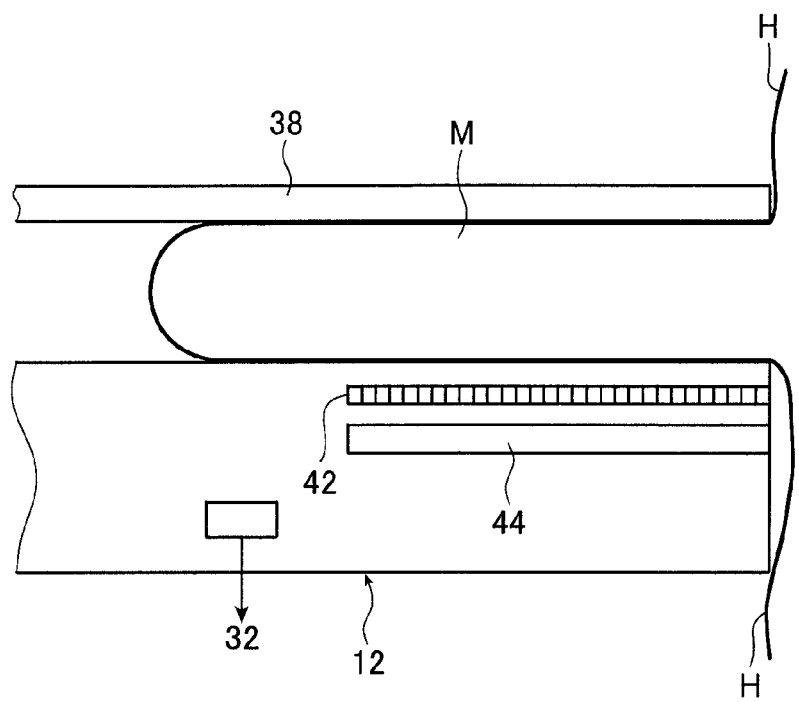
FIGS. 4A and 4B show in concept how the breast's radiation image taking apparatus shown in FIG. 1 works.
Figure 4B:
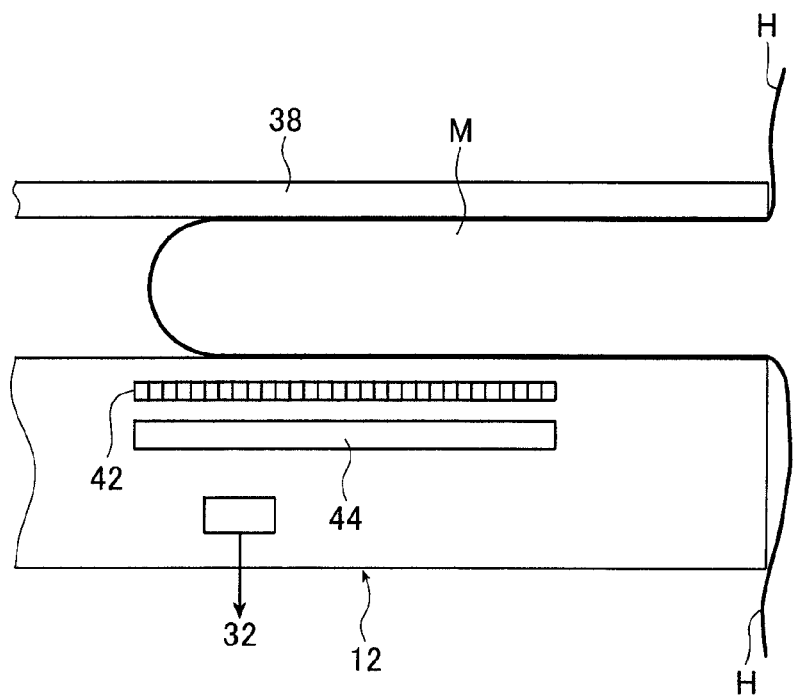

In the breast imaging apparatus 10 shown in FIG. 1, the grid 42 and the detector 44 are combined to be an integral unit which is so adapted that it can be moved to assume two specified positions, one being a position on the proximal end side that is close (preferably as close as possible) to the chest wall H of the subject and which corresponds to the imaging region on the chest wall side (or the proximal end side), as shown in FIG. 4A, and the other being a position on the distal end side that is more spaced from the chest wall H than the proximal end side and which corresponds to the imaging region on the distal end side which is at the apex side (mammary papilla side) of the breast, as shown in FIG. 4B. Thus, here again in FIG. 4, the subject (or her chest wall H) is positioned on the right side.

It should also be noted that the method of moving the grid 42 and the detector 44 is not limited in any particular way and various known methods of moving members in plate form may be employed.

In the normal imaging mode, the breast imaging apparatus 10 performs imaging only once with the detector 44 and the grid 42 being moved to the position on the proximal end side that is shown in FIG. 4A; in the split imaging mode, the breast imaging apparatus 10 performs the first imaging with the detector 44 and the grid 42 being moved to the position on the distal end side that is shown in FIG. 4B, then moves the detector 44 and the grid 42 to the position on the proximal end side that is shown in FIG. 4A, and performs the second imaging.

This point will be described later in detail.

The AEC sensor 46 is a radiation dose measuring sensor that measures the dose of radiation that passes through the breast in pre-irradiation which is performed for setting the imaging condition prior to the taking of the breast's radiation image using the detector 44.

It should be noted here that when setting the imaging condition by pre-irradiation, the breast imaging apparatus 10 may employ the detector 44 rather than the AEC sensor 46 to measure the radiation dose for setting the imaging condition. Alternatively, pre-irradiation may be omitted but the radiation dose is measured with the AEC sensor 46 during takin/taking of a radiation image of the breast in order to set the imaging condition.

While details will be given later, the breast imaging apparatus 10, if it is to be operated in the normal imaging mode, has the AEC sensor 46 disposed in a position appropriate for the setting of the imaging condition for the case of imaging where the detector 44 has been moved to the proximal end side and then the dose of radiation passing through the breast is measured; if the breast imaging apparatus 10 is to be operated in the split imaging mode, it has the AEC sensor 46 disposed in a position appropriate for the setting of the imaging condition for the case of imaging where the detector 44 has been moved to the distal end side and then the dose of radiation passing through the breast is measured.

To meet this requirement, the breast imaging apparatus 10 has a moving means (not shown) installed for moving the AEC sensor 46 to the respective positions of radiation measurement. Note that this moving means may also be of any known type of sensor moving means.

Alternatively, a plurality of AEC sensors 46 may be installed in association with those positions which are appropriate for radiation measurement for setting the imaging conditions on the proximal and distal end sides, respectively.

Note here that the positions of the AEC sensor 46 that are appropriate for the setting of the imaging conditions in association with the imaging (taking/recording) of the radiation image on both the distal and proximal end sides may be determined as appropriate for the system configuration, the sensor(s) used, the position and size of the detector 44, and other factors. Alternatively, the position of the AEC sensor 46 may be adjusted in response to the entry of a command by the operator.

On the following pages, the operation of the breast imaging apparatus 10 is described to further illustrate the present invention.

As mentioned hereinabove, the breast imaging apparatus 10 is supplied with a command for a specific imaging mode in accordance with the type of the press plate 38 attached to the vertically moving means 40.

Assume, for example, that a large press plate 38 with the size of 24×24 cm is attached; the control means 32, having received relevant information from the vertically moving means 40 learns that the current mode of imaging that has been set is that of split imaging and the control means 32 then moves the AEC sensor 46 to the position appropriate for setting the imaging condition in association with imaging on the distal end side. Furthermore, as shown schematically in FIG. 5, the control means 32 moves the detector 44 and the grid 42 to the imaging position on the distal end side which is more spaced from the chest wall H than the proximal end side; in addition, the control means 32 moves the collimator 34 to a specified position that allows the radiation from the radiation source 30 to irradiate a field of a specified region on the distal end side.

In response to the entry of a command by the operator, the press plate 38 compresses the breast M and the position information about the press plate 38 is fed to the control means 32.

The control means 32 then drives the radiation source 30 under a specified imaging condition and performs pre-irradiation; it then causes the AEC sensor 46 to measure the radiation coming through the breast M and receives the result of this measurement from the AEC sensor 46. The control means 32 learns the thickness of the breast M of interest from the position information about the press plate 38 while, at the same time, it learns the dose of radiation through the breast M from the value of radiation measurement with the AEC sensor 46, whereby the control means 32 sets the imaging condition.

In other words, the imaging condition thus set is optimum for imaging on the distal end side, or imaging the apex side of the breast M in split imaging.

Having set the imaging condition and confirmed that the detector 44 and the grid 42 have moved toward the distal end, the control means 32 drives the radiation source 30 and performs the first imaging (recording) of the radiation image of the breast M on the distal end side under the imaging condition that has been set.

Figure 5:
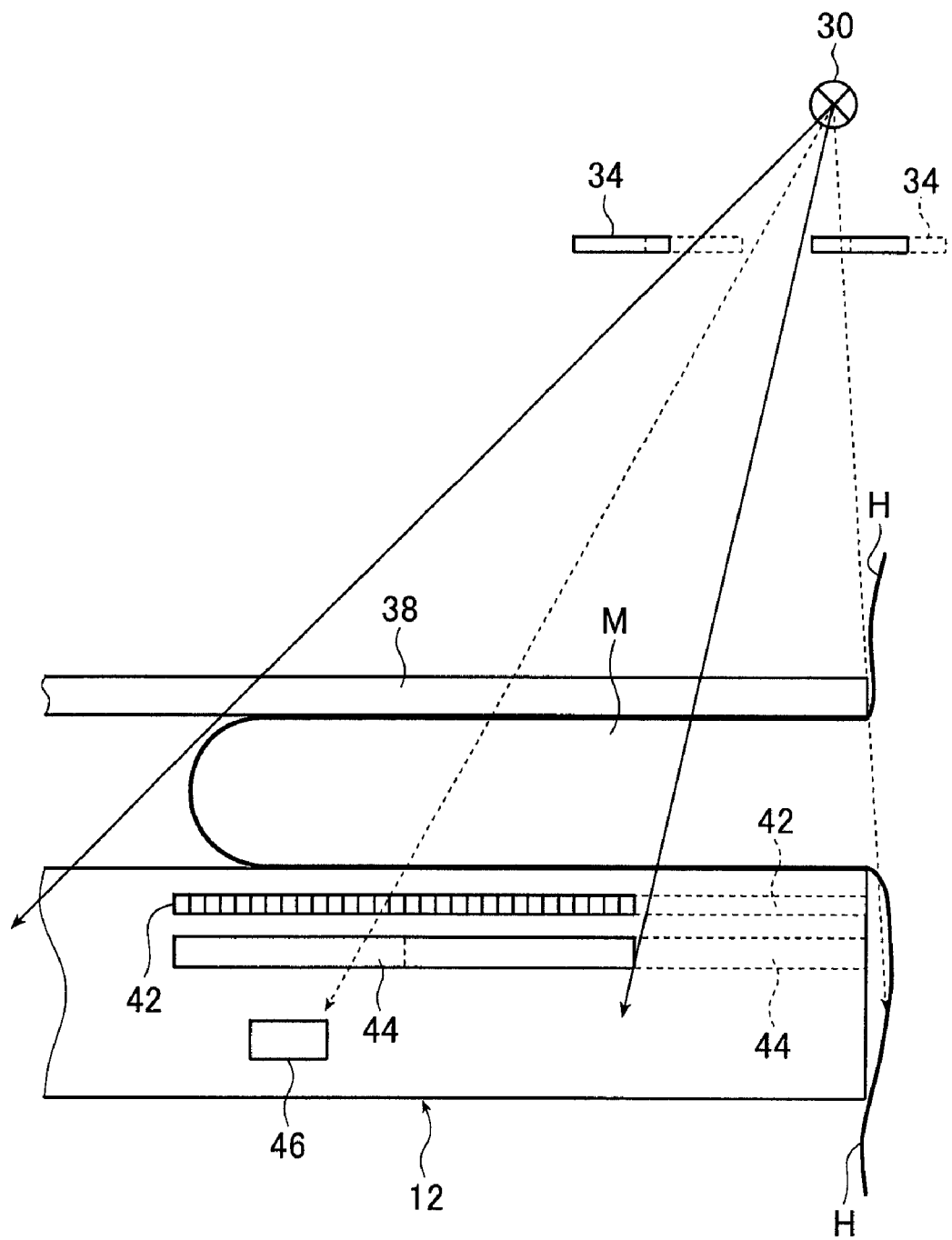
FIG. 5 shows in concept how the breast's radiation image taking apparatus shown in FIG. 1 works.

When the first imaging ends, the control means 32 moves the detector 44 and the grid 42 toward the proximal end (closer to the chest wall H) so that they are at the imaging position on the proximal end side which is indicated by the dashed lines in FIG. 5. The control means 32 also moves the collimator 34 to a specified position that allows the radiation from the radiation source 30 to irradiate a field of a specified region on the proximal end side.

Having confirmed that the detector 44, the grid 42 and the collimator 34 had moved to their specified positions, the control means 32 performs the second imaging (recording) of the radiation image of the breast M on the proximal end side under the imaging condition that was previously set in association with the distal end side. Thereafter, the compression by the press plate 38 is removed to end the split imaging of the breast M.

Assume then the case where the press plate 38 attached to the vertically moving means 40 is in the smaller size of 18×24 cm; the control means 32, having received relevant information from the vertically moving means 40 learns that the current mode of imaging that has been set is that of normal imaging.

In the taking of the radiation image of the breast M in the normal imaging mode, imaging that is the same as the second imaging on the proximal end side in the above-described split imaging mode is performed only once, except that radiation measurement by the AEC sensor 46 is performed at the position appropriate for setting the imaging condition for imaging on the proximal end side.

To be more specific, when it learns that the normal imaging mode has been set, the control means 32 moves the AEC sensor 46 to the position appropriate for setting the imaging condition for imaging on the proximal end side. In addition, the control means 32 moves the detector 44, the grid 42 and the collimator 34 to positions closer to the chest wall H that are indicated by the dashed lines in FIG. 5 which are the same as the positions for the above-described second imaging on the proximal end side in the split imaging mode.

As in the previous case, in response to the entry of a command by the operator, the press plate 38 compresses the breast M and the relevant position information is fed from the vertically moving means 40 to the control means 32, whereupon the control means 32 drives the radiation source 30 under a specified imaging condition and performs pre-irradiation; it then causes the AEC sensor 46 to measure the radiation coming through the breast M and sets the imaging condition on the basis of the position information about the press plate 38 and from the value of measurement with the AEC sensor 46. In other words, the imaging condition thus set is optimum for imaging on the proximal end side.

Having set the imaging condition and confirmed that the detector 44 and the grid 42 have moved toward the proximal end, the control means 32 drives the radiation source 30 and performs the recording of the radiation image of the breast M on the proximal end side under the imaging condition that has been set.

When imaging under this condition ends, the compression by the press plate 38 is removed to end the imaging of the breast M.

As will be apparent from the foregoing explanation, according to the present invention, the breast M, if it is so large as to extend beyond the radiation-receiving plane of the detector 44, is subjected to split imaging where it is first imaged on the distal end side in association with the apex side of the breast M and then imaged on the proximal end side in association with the area closer to the chest wall H, whereby a radiation image of all areas of the breast M can be taken in an appropriate manner. What is more, since the imaging condition that has been set in association with imaging on the distal end side is also applied to imaging on the proximal end side, the apex side of the breast M which is highly likely to contain important information can be imaged under optimum conditions; further in addition, the taken two radiation images can be examined, combined or otherwise processed in an appropriate manner.

In addition to the above-described split imaging mode, the illustrated apparatus has the normal imaging mode in which the breast is imaged only on the proximal end side and the imaging condition is set in accordance with the imaging on the proximal end side, so a radiation image of a normal-sized breast M that will not extend beyond the radiation-receiving plane of the detector 44 can also be taken in an advantageous manner.

In the present invention, the amount by which the detector 44 is moved from the proximal end side to the distal end side or vice versa in the process of split imaging (i.e., the amount by which the radiation-receiving plane of the detector 44 is moved relative to the plane on which the breast is placed) is not limited to any particular value and may be set as appropriate for various factors including the differences in physique and breast size between women to be examined.

If the detector is with the larger size of 24×24 cm, it has the advantage that the entire area of a large enough breast can be imaged in almost all cases; on the other hand, a woman of small stature can be imaged appropriately with greater ease by means of an apparatus that uses a smaller detector with the size of 18×24 cm. In addition, in order to ensure that the entire area of the breast is imaged, it is necessary that the region of the breast M to be imaged on the distal end side and the region to be imaged on the proximal end side should partly overlap in the direction in which the detector 44 is moved.

Considering this point, the amount of movement of the detector 44 is preferably no smaller than the difference in size between the smaller detector and the larger detector (which is at least 6 cm in the illustrated case) and, specifically, a range of 6 to 12 cm is preferred.

In the foregoing example, in order to reduce the amount of radiation to be applied to the subject, the radiation source 30 is fixed closest to the subject (her chest wall H) and in the case of split imaging, the collimator 34 is moved to switch the irradiation field from the distal end side to the proximal end side or vice versa.

Figure 6:
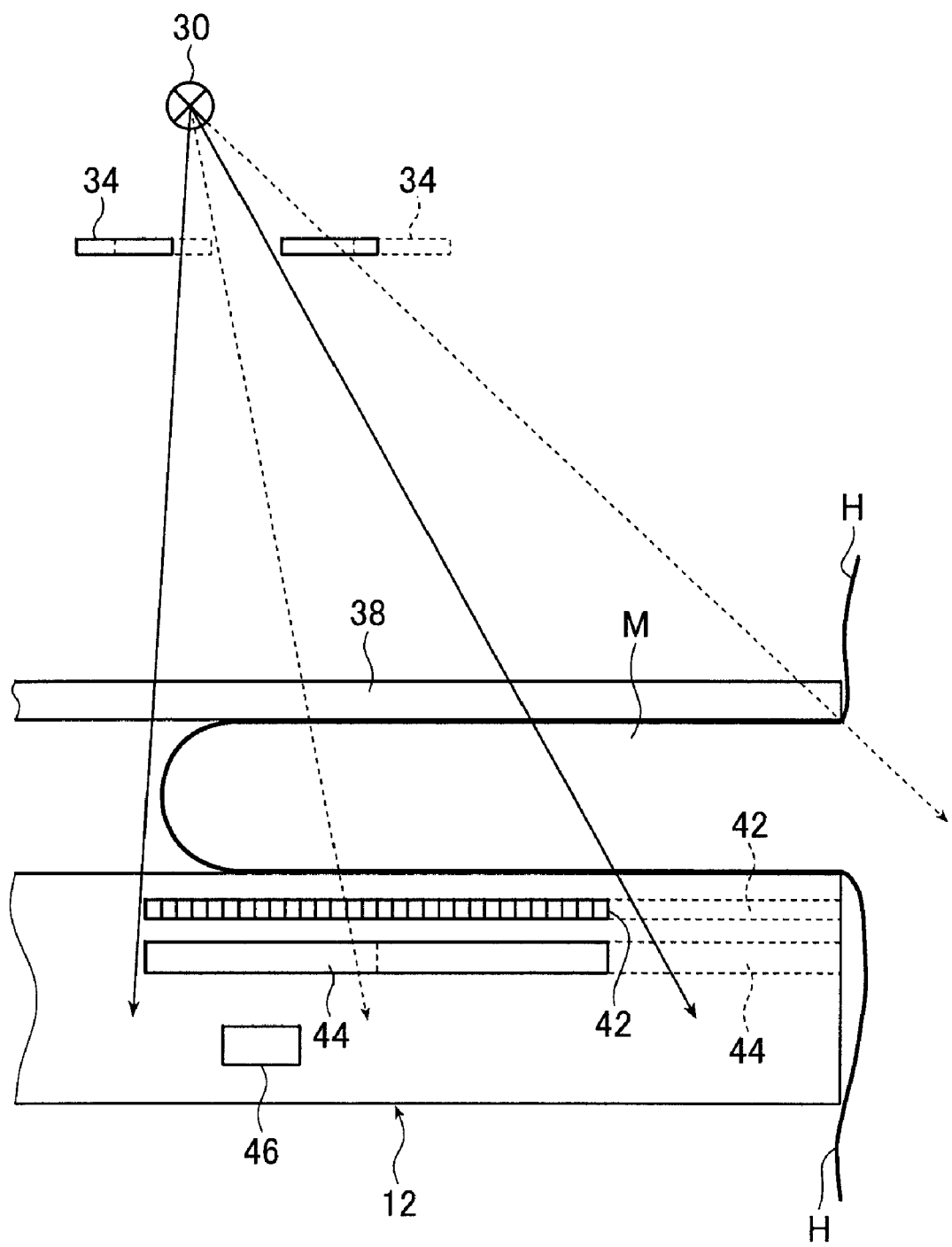
FIG. 6 shows in concept another example of the breast's radiation image taking apparatus of the present invention.

However, the present invention is by no means limited to this particular example and, as shown schematically in FIG. 6, the radiation source 30 may be fixed on the distal end side so that the irradiation field is changed by moving the collimator 34 such as to perform split imaging on the distal and proximal end sides.

According to this design, the apical portion of the breast M which is highly likely to contain important information can be irradiated just from above, so a radiation image with higher quality of the breast M can be obtained for its apical region which is critical for diagnosis.

In addition, the process of split imaging with the radiation source 30 fixed, either at the position closest to the chest wall H or on the distal end side, ensures that the radiation that has passed through the same position in the breast M is incident on the detector 44 at the same position in two takings (recordings), in other words, the image of the breast M is projected at the same position in two takings. Because of this feature, the two images obtained by split imaging can be combined easily.

Further in addition, the present invention is by no means limited to the above-described design in which split imaging is performed on the distal and proximal end sides by changing the irradiation field by means of the collimator 34 with the radiation source 30 being fixed, and the same result can be obtained by moving the radiation source 30.

Figure 7:
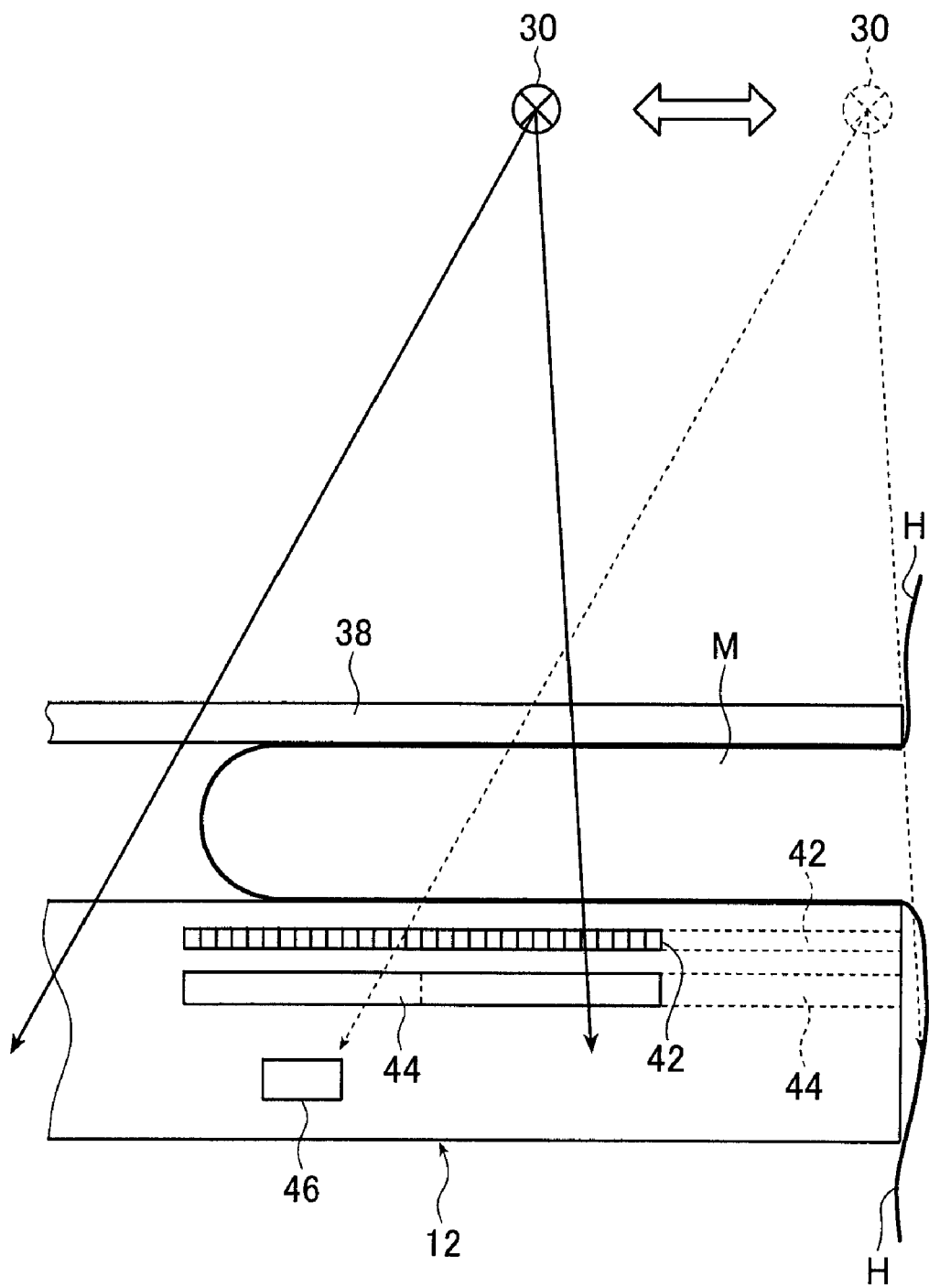
FIG. 7 shows in concept yet another example of the breast's radiation image taking apparatus of the present invention.

To be more specific, as shown schematically in FIG. 7, split imaging may be performed on the distal and proximal end sides with the irradiation field being changed by moving the radiation source 30 to the distal and proximal end sides. In FIG. 7, the collimator for delineating the irradiation field of the radiation source 30 is omitted but it should of course be possible to provide the collimator and move it en masse with the radiation source 30.

According to this design, the entire area of the breast M can be irradiated just from above, so a high-quality radiation image of the breast M can be obtained for its entire area.

It should also be noted that in order to ensure that the entire area of the breast M is imaged in the embodiment where the radiation source is moved, it is necessary that in the upper part of the breast M (namely, the part close enough to the lower surface of the press plate 38), the irradiation field on the distal end side should overlap the field on the proximal end side. This point should therefore be taken into consideration when setting the position of the detector 44, the irradiation field, and other factors.

While in the foregoing examples, two images are taken in the process of split imaging, one on the distal end side and the other on the proximal end side, by changing the position of the detector 44 and the irradiation field, this is not the sole case of the present invention and the same result can be obtained by moving the imaging table and the like, with the detector 44 and the irradiation field being fixed.

An example of this alternative design is shown in FIG. 8.

Figure 8A:
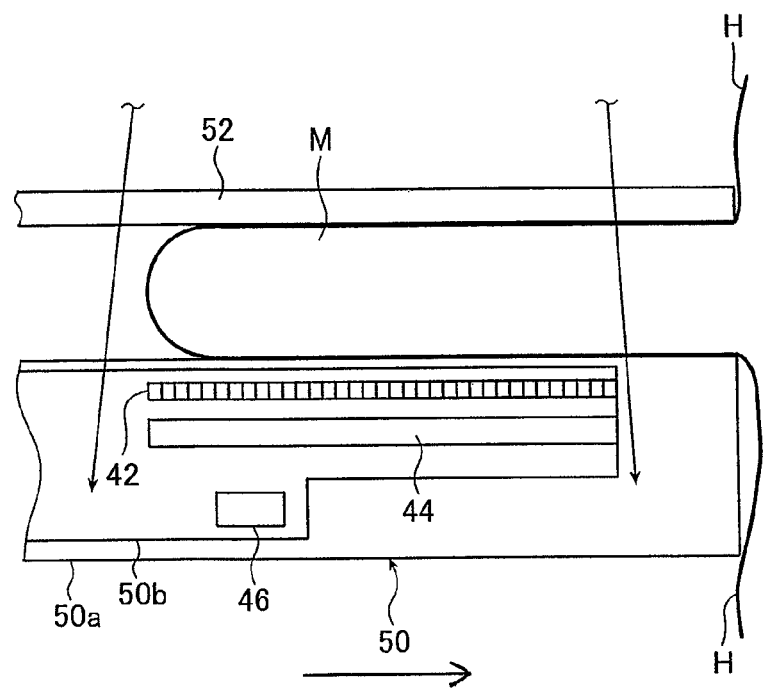
FIGS. 8A and 8B show in concept still another example of the breast's radiation image taking apparatus of the present invention.
Figure 8B:
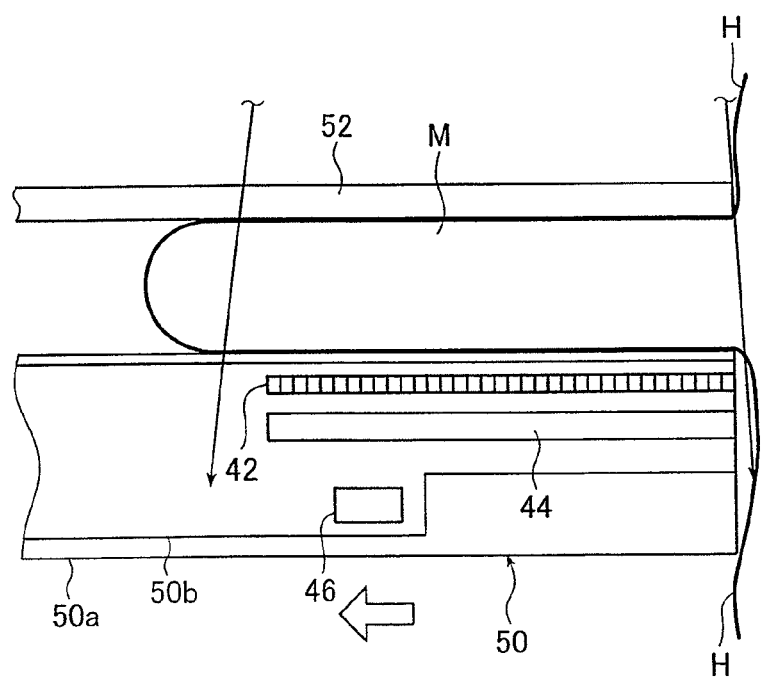

In the case shown in FIGS. 8A and 8B, the press plate 52 is adapted to be capable of moving between two positions, where one position is reached when the press plate 52 moves in a direction towards the chest wall H, as shown in FIG. 8A, and the other position is reached when the press plate 52 moves in the direction away from the chest wall H, as shown in FIG. 8B.

In addition, the imaging table 50 is of a dual structure comprising an outer casing 50a and an inner casing 50b. The outer casing 50a is adapted to be capable of moving between two positions, one that is reached when it has moved in a first direction as to push the chest wall H, as shown in FIG. 8A (to the right side) and the other that is reached when it has moved in a second, opposite direction as to pull the chest wall H, as shown in FIG. 8B (to the left side). On the other hand, the inner casing 50b is fixed and contains the detector 44, the grid 42, and the AEC sensor 46 in its interior.

In the design just described above, the upper surface of the outer casing 50a serves as the plane on which the breast M is placed.

Consequently, in the state shown in FIG. 8A, which is obtained when the imaging table 50 has moved to a position that is reached when the imaging table 50 has moved in the first direction as to push the chest wall H, the fixed detector 44 is spaced from the chest wall H and at the position that corresponds to the apical portion of the breast M whereas in the state shown in FIG. 8B which is obtained when the imaging table 50 has moved to another position that is reached when the imaging table 50 has moved in the second direction as to pull the chest wall H, the fixed detector 44 is close enough to the chest wall H and at the position that corresponds to the proximal end portion of the breast M.

In the design under consideration, the state shown in FIG. 8A which is obtained when the outer casing 50a and the press plate 52 have moved in the direction in which they push the chest wall H is the state in which the fixed detector 44 is spaced from the chest wall H and this allows for imaging on the distal end side.

To be more specific, in the state shown in FIG. 8A where the imaging position is on the distal end side, pre-irradiation is performed and in accordance with the value of measurement with the AEC sensor 46 and the position of the press plate 52, namely, the thickness of the breast M, the imaging condition is set and under this condition, the first imaging of the breast M is performed on the distal end side.

When the first imaging ends, the outer casing 50a and the press plate 52 are moved in the direction in which they pull the chest wall H until the detector 44 is at the position on the proximal end side which is shown in FIG. 8B and in this state, the second imaging of the breast M is performed under the same imaging condition as set for the first imaging.

While the breast's radiation image taking apparatus and method of the present invention have been described above in detail, the present invention is by no means limited to the foregoing embodiments and various improvements and modifications can of course be made without departing from the scope and spirit of the present invention.

What is claimed is:

1. A breast's radiation image taking apparatus, comprising:
a radiation source for irradiating a breast of a subject;
a breast support plane on which said breast is to be placed;
a radiation-receiving plane for acquiring a radiation image of said breast;
an imaging position switching means for switching relative positions of said breast support plane and said radiation-receiving plane so that a position of said radiation-receiving plane is switched between a proximal end side, which is near a chest wall of said subject, and a distal end side, which is more spaced from said chest wall than said proximal end side;
an imaging mode setting means for setting one of two imaging modes, one imaging mode being a split imaging mode for acquiring an image of a breast of a larger size in which a first radiation image is taken with the radiation-receiving plane positioned on the distal end side and then a second radiation image is taken with the radiation-receiving plane positioned on the proximal end side and other imaging mode being a normal imaging mode for acquiring an image of a breast of a smaller size in which only one radiation image is taken with the radiation-receiving plane positioned on the proximal end side;
an imaging condition setting means for setting a first imaging condition on the distal end side when said split imaging mode is set by said imaging mode setting means, and for setting a second imaging condition between the distal end side and the proximal end side when said normal imaging mode is set by said imaging mode setting means; and an imaging control means for controlling said imaging position switching means to switch said position of said radiation-receiving plane from said distal end side to said proximal end side so that the first radiation image and the second radiation image are taken in two positions on the distal and proximal end sides, respectively, under the first imaging condition when said split imaging mode is set by said imaging mode setting means and for controlling said imaging position switching means to position said radiation-receiving plane on the proximal side so that the only one radiation image is taken in a single position on the proximal end side under the second imaging condition when said normal imaging mode is set by said imaging mode setting means.

2. The breast's radiation image taking apparatus according to claim 1, wherein said imaging control means performs first imaging of the first radiation image with said radiation-receiving plane positioned on said distal end side, then allows said imaging position switching means to switch said position of said radiation-receiving plane, and performs second imaging of the second radiation image with said radiation-receiving plane positioned on said proximal end side, when said split imaging mode is set by said imaging mode setting means.

3. The breast's radiation image taking apparatus according to claim 1, wherein said imaging position switching means switches said position of said radiation-receiving plane as relative to said breast support plane by moving said radiation-receiving plane.

4. The breast's radiation image taking apparatus according to claim 1, wherein an imaging region on said proximal end side partly overlaps an imaging region on said distal end side by a specified amount.

5. The breast's radiation image taking apparatus according to claim 1, further comprising:
an imaging table having an upper surface which serves as said breast support plane.

6. The breast's radiation image taking apparatus according to claim 5, further comprising:
a detector contained in an interior of said imaging table, said detector having a receiving plane which serves as said radiation-receiving plane.

7. The breast's radiation image taking apparatus according to claim 1, further comprising:
a detector having a receiving plane which serves as said radiation-receiving plane.

8. The breast's radiation image taking apparatus according to claim 7, wherein said detector is an imaging medium for recording the radiation image.

9. The breast's radiation image taking apparatus according to claim 7, wherein said detector is a radiation image conversion panel utilizing a stimulable phosphor or a flat panel detector for acquiring said radiation image by radiation-to-image conversion.

10. The breast's radiation image taking apparatus according to claim 7, wherein the detector includes a flat panel detector comprising M×N array of detection elements, which convert the radiation from the radiation source impinging on the radiation-receiving plane of the detector into electrical signals.

11. The breast's radiation image taking apparatus according to claim 7, wherein the radiation-receiving plane of the detector is disposed substantially parallel and proximate to the breast support plane.

12. The breast's radiation image taking apparatus according to claim 11, wherein the imaging switching means moves the detector longitudinally, in a direction substantially parallel to the breast support plane and wherein the radiation source is moved based on moving of the detector.

13. The breast's radiation image taking apparatus according to claim 1, wherein the only one radiation image captures an image of an entire breast.

14. A breast's radiation image taking method, comprising:
placing a breast of a subject on a breast support plane;
setting one of two imaging modes, one imaging mode being a split imaging mode for acquiring an image of a breast of a larger size in which a first radiation image is taken with a radiation-receiving plane positioned on a distal end side, which is an imaging region spaced from a chest wall of said subject, and then a second radiation image is taken with the radiation-receiving plane positioned on a proximal end side closer to said chest wall than said distal end side and other imaging mode being a normal imaging mode for acquiring an image of a breast of a smaller size in which only one radiation image is taken with the radiation-receiving plane being positioned on said proximal end side;
setting a first imaging condition on the distal end side when said split imaging mode is set, and setting a second imaging condition between the distal end side and the proximal end side when said normal imaging mode is set; and
taking the first radiation image and the second radiation image in two positions on said distal and proximal end sides, respectively, under the first imaging condition when said split imaging mode is set and taking the only one radiation image in a single position on the proximal end side under the second imaging condition when said normal imaging mode is set.

15. The breast's radiation image taking method according to claim 14, further comprising:
changing an imaging region from said first region to said second region by changing relative positions of said breast support plane and said radiation-receiving plane between first imaging in said first region and second imaging in said second region.

16. The breast's radiation image taking method according to claim 15, wherein said relative positions of said breast support plane and said radiation-receiving plane are changed by moving said radiation-receiving plane from a first position associated with said first region to a second position associated with said second region.

17. The breast's radiation image taking method according to claim 14, wherein said second region partly overlaps said first region by a specified amount.

18. The breast's radiation image taking method according to claim 14, wherein the only one radiation image captures an image of an entire breast.

* * * * *